US00PP34096P2

(12) United States Plant Patent
Rinehart

(10) Patent No.: US PP34,096 P2
(45) Date of Patent: Apr. 5, 2022

(54) POINSETTIA PLANT NAMED 'RINEBOB'

(50) Latin Name: ***Euphorbia pulcherrima* Willd.**
Varietal Denomination: Rinebob

(71) Applicant: Steven Earl Rinehart, Encinitas, CA (US)

(72) Inventor: Steven Earl Rinehart, Encinitas, CA (US)

( * ) Notice: Subject to any disclaimer, the term of this patent is extended or adjusted under 35 U.S.C. 154(b) by 0 days.

(21) Appl. No.: 17/390,932

(22) Filed: Jul. 31, 2021

(51) Int. Cl.
*A01H 5/12* (2018.01)
*A01H 6/38* (2018.01)

(52) U.S. Cl.
USPC ..... Plt./304

(58) Field of Classification Search
None
See application file for complete search history.

*Primary Examiner* — Susan McCormick Ewoldt
(74) *Attorney, Agent, or Firm* — C. Anne Whealy

(57) ABSTRACT

A new and distinct cultivar of *Poinsettia* plant named 'Rinebob', characterized by its upright to somewhat outwardly and uniformly mounded plant habit; vigorous growth habit; freely and upright to somewhat outwardly branching habit; dark green-colored leaves; plants flower on or about November 18 in Southern California when grown under natural season conditions; broad and horizontal flower bracts that are light greenish white to white in color; numerous cyathia per inflorescence; and good post-production longevity.

2 Drawing Sheets

Figure 1:
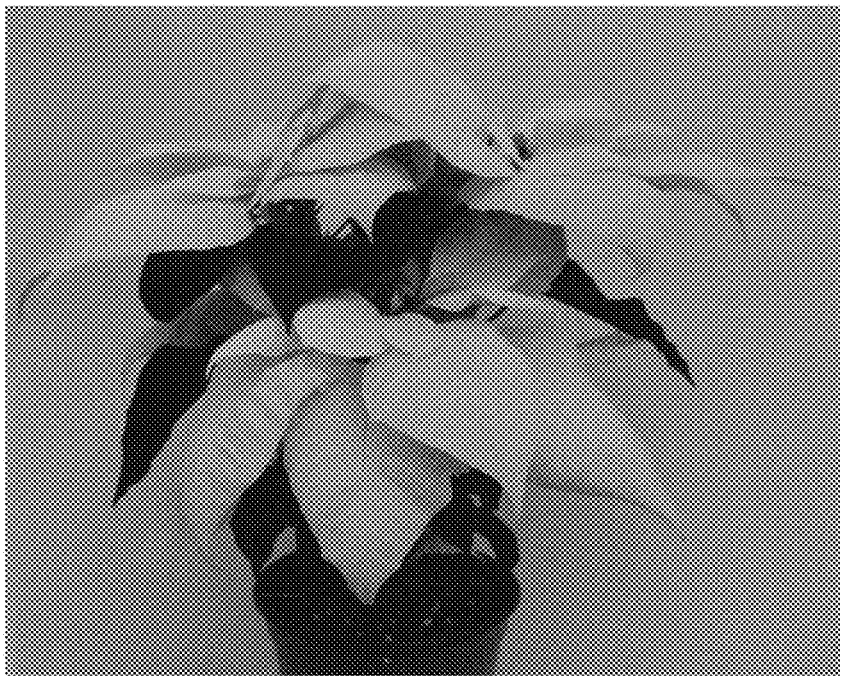

Botanical designation: *Euphorbia pulcherrima* Willd.
Cultivar denomination: 'RINEBOB'.

STATEMENT REGARDING PRIOR DISCLOSURES BY INVENTOR/APPLICANT

The Inventor/Applicant assert that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant hereby claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Poinsettia* plant, botanically known as *Euphorbia pulcherrima* Wild., and hereinafter referred to by the cultivar name 'Rinebob'.

The new *Poinsettia* plant is a product of a planned breeding program conducted by the Inventor in Bonsall, Calif. The objective of the breeding program is to create new early-flowering *Poinsettia* plants having white-colored flower bracts and excellent post-production longevity.

The new *Poinsettia* plant originated from a cross-pollination made by the Inventor in January, 2016 of a proprietary selection of *Euphorbia pulcherrima* Willd. identified as code number 14-990, not patented, as the female, or seed, parent, with *Euphorbia pulcherrima* Willd. 'Rineal', disclosed in U.S. Plant Pat. No. 32,633, as the male, or pollen, parent. The new *Poinsettia* plant was discovered and selected by the Inventor as a single flowering plant from within the progeny of the stated cross-pollination in a controlled greenhouse environment in Bonsall, Calif. in November, 2016.

Asexual reproduction of the new *Poinsettia* plant by terminal vegetative cuttings in a controlled greenhouse environment in Bonsall, Calif. since April, 2017 has shown that the unique features of this new *Poinsettia* plant are stable and reproduced true to type in successive generations of asexual reproduction.

SUMMARY OF THE INVENTION

Plants of the new *Poinsettia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Rinebob'. These characteristics in combination distinguish 'Rinebob' as a new and distinct *Poinsettia* plant:

1. Upright to somewhat outwardly and uniformly mounded plant habit.
2. Vigorous growth habit.
3. Freely and upright to somewhat outwardly branching habit.
4. Dark green-colored leaves.
5. When grown under natural flowering season conditions plants flower on or about November 18 in Southern California.
6. Broad and horizontal flower bracts that are light greenish white to white in color.
7. Numerous cyathia develop per inflorescence.
8. Good post-production longevity.

In side-by-side comparisons conducted in Bonsall, Calif., plants of the new *Poinsettia* differ primarily from plants of the female parent selection in the following characteristics:

1. Plants of the new *Poinsettia* are larger than plants of the female parent selection.
2. Plants of the new *Poinsettia* have larger flower bracts than plants of the female parent selection.
3. Flower bracts of plants of the new *Poinsettia* are not as bright white in color as flower bracts of plants of the female parent selection.
4. Plants of the new *Poinsettia* have better postproduction longevity than plants of the female parent selection.

In side-by-side comparisons conducted in Bonsall, Calif., plants of the new *Poinsettia* differ primarily from plants of the male parent, 'Rineal', in the following characteristics:

1. Plants of the new *Poinsettia* are broader than and not as upright as plants of 'Rineal'.
2. Leaves of plants of the new *Poinsettia* are darker green in color than leaves of plants of 'Rineal'.
3. Flower bracts of plants of the new *Poinsettia* are broader and more horizontal (not as upright) as flower bracts of plants of 'Rineal'.

Plants of the new *Poinsettia* can be compared to plants of the *Euphorbia pulcherrima* Willd. 'Fispue White', disclosed in U.S. Plant Pat. No. 13,659. In side-by-side comparisons, plants of the new *Poinsettia* differ primarily from plants of 'Fispue White' in the following characteristics:

1. Plants of the new *Poinsettia* are larger than and not as compact as plants of 'Fispue White'.
2. Plants of the new *Poinsettia* have larger flower bracts than plants of 'Fispue White'.
3. Flower bracts of plants of the new *Poinsettia* are more white in color than flower bracts of plants of 'Fispue White'.

BRIEF DESCRIPTION OF THE PHOTOGRAPHS

The accompanying photographs illustrate the overall appearance of the new *Poinsettia* plant showing the colors as true as it is reasonably possible to obtain in colored reproductions of this type. Colors in the photographs may differ slightly from the color values cited in the detailed botanical description which accurately describe the colors of the new *Poinsettia* plant.

The photograph on the first sheet (FIG. 1) is a side perspective view of a typical flowering plant of 'Rinebob' grown in a container.

Figure 2:
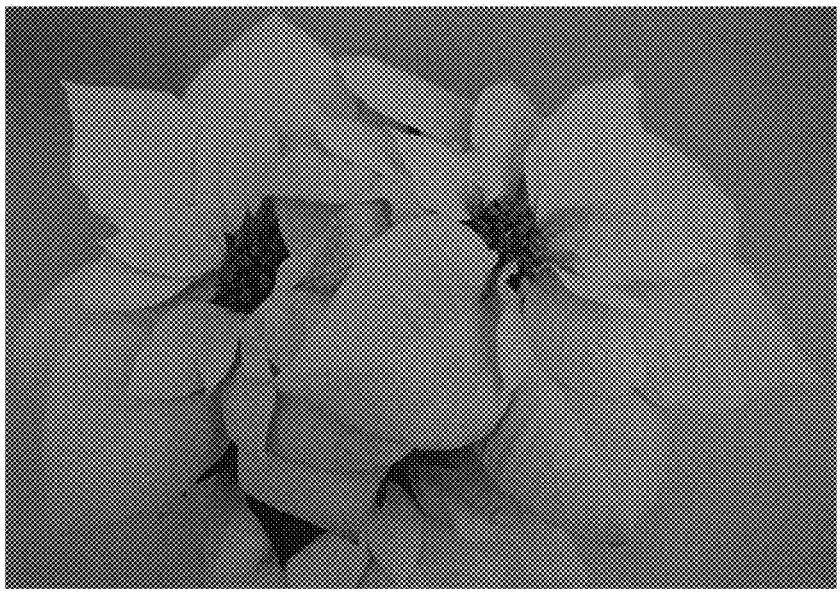

The photograph on the second sheet (FIG. 2) is a close-up view of a typical flowering plant of 'Rinebob'.

DETAILED BOTANICAL DESCRIPTION

Plants used in the aforementioned photographs and in the following detailed description were grown during the autumn and winter in 15.25-cm containers in a polyethylene-covered greenhouse in Encinitas, Calif. under natural season conditions and cultural practices typical of commercial *Poinsettia* production. During the production of the plants, day temperatures ranged from 24° C. to 26° C., night temperatures averaged 18° C. and light levels ranged from 5,000 to 6,000 foot-candles. Plants were pinched one time and were five months from unrooted cuttings when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. 'Rinebob'.

Parentage:

*Female, or seed, parent.*—Proprietary selection of *Euphorbia pulcherrima* Willd. identified as code number 14-990, not patented.

*Male, or pollen, parent.*—*Euphorbia pulcherrima* Willd. 'Rineal', disclosed in U.S. Plant Pat. No. 32,633.

Propagation:

*Type.*—Terminal vegetative cuttings.

*Time to initiate roots, summer.*—About ten days at temperatures about 21° C.

*Time to initiate roots, winter.*—About ten days at temperatures about 19° C.

*Time to produce a rooted young plant, summer.*—About 26 days at temperatures about 21° C.

*Time to produce a rooted young plant, winter.*—About 28 days at temperatures about 19° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to somewhat outwardly spreading and uniformly mounded plant habit; broad inverted triangle; inflorescences with numerous flower bracts positioned above the foliar plane; vigorous growth habit and moderate growth rate.

*Plant height.*—About 34 cm.

*Plant diameter or spread.*—About 47.5 cm.

*Lateral branch description.*—Branching habit: Freely branching habit, about seven lateral branches develop after pinching; upright to somewhat outwardly branching habit. Length: About 27 cm. Diameter: About 7 mm. Internode length: About 2 cm. Strength: Strong. Aspect: About 30° to 40° from vertical. Texture and luster: Smooth, glabrous; glossy. Color: Close to between 146A and 146B.

*Leaf description.*—Arrangement: Alternate, simple. Length: About 13 cm. Width: About 9.5 cm. Shape: Broadly ovate. Apex: Acuminate. Base: Truncate with obtuse tendencies. Margin: Entire. Aspect: Outwardly to slightly drooping with development. Texture and luster, upper surface: Smooth, glabrous; slightly glossy. Texture and luster, lower surface: Glabrous; prominent venation; matte. Venation pattern: Pinnate, arcuate. Color: Developing leaves, upper surface: Darker green than 147A. Developing leaves, lower surface: Close to 147B. Fully expanded leaves, upper surface: Darker green than N189A; venation, close to 146A and 147A. Fully expanded leaves, lower surface: Close to 147B; venation, close to 146B to 146C. Leaf petioles: Length: About 5.5 cm. Diameter: About 3 mm by 3.5 mm. Texture and luster, upper and lower surfaces: Smooth, glabrous; semi-glossy. Color, upper and lower surfaces: Close to 146B.

Inflorescence description:

*Inflorescence type and habit.*—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower on or about November 18 in Southern California; under artificial long nyctoperiod/short photoperiod conditions, plants flower about eight weeks later.

*Post-production longevity*.—Good post-production longevity; plants of the new *Poinsettia* maintain good substance and flower bract color for about six weeks under interior conditions; flower bracts persistent and cyathia not persistent.

*Inflorescence diameter*.—About 29 cm to 33 cm.

*Inflorescence height* (*depth*).—About 10.5 cm.

*Flower bracts*.—Quantity per inflorescence: Numerous, about 30. Length, largest bracts: About 15 cm. Width, largest bracts: About 10 cm. Shape: Broadly ovate. Apex: Acuminate. Base: Obtuse to truncate. Margin: Mostly entire. Aspect: Slightly upright to mostly horizontal, older flower bracts slightly drooping with development. Texture and luster, upper surface: Smooth, glabrous; matte. Texture and luster, lower surface: Glabrous with prominent venation; matte. Venation pattern: Pinnate, arcuate. Color: Transitional bracts, upper surface: Close to 4D variably tinged with close to 144A. Transitional bracts, lower surface: Close to 4D slightly tinged with close to 144C. Developing bracts, upper and lower surfaces: Close to 158D. Fully expanded bracts, upper and lower surfaces: Close to 155A to 155B; venation, similar to lamina; color does not change with development. Bract petioles: Length: About 3.75 cm. Diameter: About 2.5 mm by 3 mm. Texture and luster, upper and lower surfaces: Smooth, glabrous; semi-glossy. Color, upper and lower surfaces: Close to 145A.

*Cyathia*.—Quantity per corymb: About 15 to 18. Length: About 1.4 cm. Width: About 6 mm. Shape: Ovoid. Texture and luster: Smooth, glabrous; slightly glossy. Color, inner surface: Close to 146B to 146C. Color, outer surface: Close to 144A to 144B.

*Nectaries*.—Quantity per cyathium: One. Length: About 7.5 mm. Width: About 4 mm. Shape: Fan-shaped. Texture and luster: Smooth, glabrous; slightly glossy. Color, inner and outer surfaces: Close to 13A.

*Peduncles*.—Length: About 5 mm to 7 mm. Diameter: About 2.5 mm. Strength: Strong. Aspect: Mostly upright to outwardly. Texture and luster: Smooth, glabrous; matte. Color: Close to 144A to 144B.

*Reproductive organs*.—Stamens: Quantity per cyathium: About 20 to 24. Filament length: About 5 mm to 7 mm. Filament color: Close to 145D. Anther shape: Round to oval; bi-lobed. Anther length: About 1.25 mm. Anther color: Close to 13A. Amount of pollen: Scarce to moderate. Pollen color: Close to 13A. Pistils: Quantity per cyathium: One; tri-parted. Pistil length: About 8.5 mm. Stigma shape: Lanceolate, six-parted, recurved. Stigma color: Close to 144A. Style length: About 3 mm. Style color: Close to 145B to 145D. Ovary color: Close to 145D.

*Seeds and fruits*.—To date, seed and fruit production have not been observed on plants of the new *Poinsettia*.

Pathogen & pest resistance: To date, plants of the new *Poinsettia* have been observed to be relatively resistant to *Botrytis*. Plants have not been shown to be resistant to pests and other pathogens common to *Poinsettia* plants.

Temperature tolerance: Plants of the new *Poinsettia* have been observed to tolerate temperatures ranging from about 13° C. to about 32° C.

It is claimed:

1. A new and distinct *Poinsettia* plant named 'Rinebob' as illustrated and described.

* * * * *